(12) United States Patent
Huo et al.

(10) Patent No.: US 7,746,976 B2
(45) Date of Patent: Jun. 29, 2010

(54) BONE MINERAL DENSITY ASSESSMENT USING MAMMOGRAPHY SYSTEM

(75) Inventors: Zhimin Huo, Pittsford, NY (US); Chang-Ying J. Yang, Webster, NY (US); Mark S. Purdum, Ontario, NY (US)

(73) Assignee: Carestream Health, Inc., Rochester, NY (US)

( * ) Notice: Subject to any disclaimer, the term of this patent is extended or adjusted under 35 U.S.C. 154(b) by 118 days.

(21) Appl. No.: 11/614,199

(22) Filed: Dec. 21, 2006

(65) Prior Publication Data

US 2007/0153973 A1 Jul. 5, 2007

Related U.S. Application Data

(60) Provisional application No. 60/755,233, filed on Dec. 30, 2005.

(51) Int. Cl.
*G01N 23/087* (2006.01)

(52) U.S. Cl. .............................. 378/54; 378/53; 378/56; 378/98.9

(58) Field of Classification Search .................... 378/37, 378/51, 53, 54, 55, 56, 156, 157, 158, 159, 378/98.9, 98.11, 207
See application file for complete search history.

(56) References Cited

U.S. PATENT DOCUMENTS

| | | | |
|---|---|---|---|
| 3,515,874 A | | 6/1970 | Bens et al. |
| 5,033,075 A | * | 7/1991 | DeMone et al. ............. 378/156 |
| 5,396,532 A | * | 3/1995 | Aichinger et al. ........... 378/112 |
| 5,528,043 A | | 6/1996 | Spivey et al. |
| 5,712,892 A | | 1/1998 | Weil et al. |
| 5,886,353 A | * | 3/1999 | Spivey et al. .......... 250/370.09 |
| 5,898,753 A | * | 4/1999 | Schick et al. ................. 378/54 |
| 5,912,944 A | * | 6/1999 | Budinski et al. ............ 378/182 |
| 5,917,877 A | * | 6/1999 | Chiabrera et al. ........... 378/207 |
| 6,246,745 B1 | | 6/2001 | Bi et al. |
| 6,516,045 B2 | * | 2/2003 | Shepherd et al. .............. 378/53 |
| 6,632,020 B2 | * | 10/2003 | Kaufhold et al. ............ 378/207 |
| 6,816,564 B2 | | 11/2004 | Charles, Jr. et al. |
| 7,203,274 B2 | * | 4/2007 | Charles et al. ................ 378/54 |
| 7,387,439 B2 | * | 6/2008 | Yang et al. .................. 378/207 |
| 7,488,109 B2 | * | 2/2009 | Hangartner et al. ......... 378/207 |
| 2005/0031181 A1 | | 2/2005 | Bi et al. |

(Continued)

FOREIGN PATENT DOCUMENTS

EP          0 322 260          6/1989

(Continued)

*Primary Examiner*—Allen C. Ho (57) ABSTRACT

A method and system for determining the bone mineral density of a body extremity. An image of a body extremity is acquired using a mammography x-ray system whereby a bone mineral density can be performed on the image. The system for determining the bone mineral density of a body extremity includes: a support for supporting the body extremity; a detector for capturing an image of the body extremity; and an x-ray source adapted to project an x-ray beam through the body extremity toward the detector, the x-ray source having a voltage of no more than about 45 kVp and having a target/filter combination of rhodium/rhodium, molybdenum/molybdenum, molybdenum/rhodium, or tungsten/rhodium. An attenuation filter separate from the target/filter combination may be provided between the source and the body extremity, between the body extremity and the detector, or both.

20 Claims, 4 Drawing Sheets

U.S. PATENT DOCUMENTS

2005/0059875 A1  3/2005  Chung et al.

FOREIGN PATENT DOCUMENTS

| | | |
|---|---|---|
| EP | 0 379 629 | 8/1990 |
| FR | 2 717 367 | 9/1995 |
| GB | 1381744 | 1/1975 |
| WO | WO2006/055942 | 5/2006 |

* cited by examiner

BONE MINERAL DENSITY ASSESSMENT USING MAMMOGRAPHY SYSTEM

CROSS REFERENCE TO RELATED APPLICATIONS

Reference is made to, and priority is claimed from, commonly assigned U.S. Provisional Patent Application No. 60/755,233, entitled "BONE MINERAL DENSITY ASSESSMENT USING MAMMOGRAPHY SYSTEM", provisionally filed on Dec. 30, 2005 in the name of Huo et al.

FIELD OF THE INVENTION

The invention relates generally to the field of mammography imaging system. More specifically, the invention relates to a system for assessing Radiation Absorptiometry (RA) based BMD (Bone Mineral Density) using a mammography x-ray imaging system.

BACKGROUND OF THE INVENTION

Osteoporosis is a skeletal disorder characterized by reduced bone strength. It can result in increased risk to factures, height loss, hunched backs, and pain. Bone strength is a function of bone mineral density (BMD) and bone quality. It is believed that bone mineral density peaks about the age of 30 for both men and women, and then declines gradually. Some statistics have indicated that osteoporosis affects approximately 20 million people and is a cause of about 1.3 million fracture incidents in the United States each year. As such, screening for bone mineral density is often desired.

Several common techniques have been used to measure bone mineral density, including bone puncture, radiation absorptiometry of single energy x-ray systems, DEXA (dual energy x-ray absorptiometry), and sonography.

Bone puncture can be an accurate but invasive procedure, which involves the extraction of bone mass from spine area. This procedure carries risk.

With regard to single energy x-ray systems, mineral loss in a person's bones can be estimated from a single energy x-ray image of a body part. In diagnosing and treating bone diseases, it is common to take radiographic images of the patient (e.g., skeletal features of the patient), then either read the images directly or perform software analysis on the images to extract information of interest. For example, in diagnosing or monitoring the treatment of osteoporosis, one might take x-ray images of selected skeletal bones, then perform computer analysis on certain image features to determine bone volume, bone length, bone geometric changes, bone strength conditions, bone age, bone cortical thickness, and bone mineral mass.

Typically for reading and interpreting radiographic images directly, the treating physician will refer the patient to a radiologist, who can supervise both taking the radiographic image and interpreting the image to extract desired bone information, such as bone mass and bone contour irregularities. Alternatively, if the bone analysis is done, at least partially, by a computer analysis system, the x-ray images prepared by the radiologist may be sent back to the treating physician's computer site or to another computer site for computer analysis.

DEXA is a device used by the hospitals to measure bone mineral density (BMD). In DEXA, two low-dosage x-ray beams with differing energy levels are aimed at the patient's spine, hip or whole body using conventional x-ray machines. The computer calculates the content of bone mineral density based on the relationship that different bones absorb different energy levels. Some consider DEXA to be accurate, but the apparatus is bulky and expensive and results in more radiation to the patients. U.S. Pat. No. 6,816,564 (Charles, Jr.) is directed to a technique for deriving tissue structure from multiple projection dual-energy x-ray absorptiometry.

Sonography devices measure the bone mineral density of peripheral bones, such as heel, shin bone, and kneecap. But it is recognized that the bone mineral density in the spine or hip change faster than that in heel, shin bone, or kneecap. Thus sonography is considered by some to be not as accurate or sensitive as DEXA in the determination of bone mineral density. DEXA allows early detection of abnormal change in bone mass for its targets spine, hip, or whole body. However, sonography offers advantages of lower cost and radiation-free.

U.S. Pat. No. 6,246,745 (Bi) describes a software system for determining bone mineral density from radiographic images of a patient hand obtained from conventional x-ray imaging system.

US Patent Application No. 2005/0059875 (Chung) describes a biosensor and method for bone mineral density measurement.

US Patent Application No. 2005/0031181 (Bi) is directed to a system and method for analyzing bone conditions using DICOM compliant bone radiographic images.

U.S. Pat. No. 5,712,892 (Weil), commonly assigned, is directed to an apparatus for measuring the bone mineral content of an extremity.

While such systems may have achieved certain degrees of success in their particular applications, there is a need for a system and method for bone mineral density screening, particularly wherein a medical professional can readily and locally (e.g., at their office location) generate a bone mineral density report. A suitable system would be easy to use, reduced in cost, yet provide sufficient accuracy. Preferred would be an on-site screening that can be utilized by physicians, radiologists, or other medical professionals.

SUMMARY OF THE INVENTION

An object of the present invention is to provide an imaging system and method to acquire hand x-ray images suitable for bone mineral density (BMD) screening and analysis using a mammography x-ray imaging system.

Any objects provided are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided a mammography x-ray imaging system adapted to acquire hand images with sufficient image quality for the assessment of BMD by a computer-aided system.

According to one aspect of the invention, the system includes an x-ray generator, x-ray source/target, filtration, x-ray detector, and a template for positioning the hand.

According to another aspect of the present invention, there is provided a method of positioning the hand to obtain hand images with sufficient image quality for bone mineral density assessment.

According to another aspect of the present invention, there is provided a preferred range of kVp (x-ray energy) and mAs (exposure) for a given target/filtration (built in a mammography x-ray image system) combination to obtain sufficient quality hand images when mammography screen/film systems are used as an image detector.

According to another aspect of the present invention, there is provided a method of converting analog images to digital images for computer analysis. A film digitizer with a preferred dynamic range can be employed to convert analog images to digital images for the computer analysis.

An image of a body extremity is acquired using a mammography x-ray system whereby a bone mineral density assessment can be performed on the image. The system for determining the bone mineral density of a body extremity includes: a support for supporting the body extremity; a detector for capturing an image of the body extremity; and an x-ray source adapted to project an x-ray beam through the body extremity toward the detector, the x-ray source having a voltage of no more than about 45 kVp and having a target/filter combination of rhodium/rhodium, molybdenum/molybdenum, molybdenum/rhodium, or tungsten/rhodium. An attenuation filter separate from the target/filter combination may be provided between the source and the body extremity, between the body extremity and the detector, or both.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE INVENTION

The following is a detailed description of the preferred embodiments of the invention, reference being made to the drawings in which the same reference numerals identify the same elements of structure in each of the several figures.

It is noted that the American Cancer Society recommends that women over the age of 40 years obtain annual mammograms. Millions of women have their annual screening mammograms each year at hospitals or breast imaging centers. Accordingly, Applicants have noted it would be desirable for women to have both their annual mammography screening and a bone mineral density screening done in one visit, at one location, and using one imaging system.

Conventionally, extremities (e.g., hands and feet) are imaged using conventional x-ray system, which generates an x-ray beam adapted to capture both low and high-density objects (i.e., bone and soft tissue) on a detector (film or digital) that are designed with a wide dynamic range.

In contrast, mammography imaging systems are configured for high contrast (i.e., narrow dynamic range) to image the soft tissue in the breast for the purpose of detection and diagnosis of breast cancer.

The present invention is directed to a system and method for acquiring hand images using a mammography x-ray imaging system. A treating physician or a computer-aided system can then analyze the acquired images for bone mineral density (BMD) loss assessment. It is intended that the use of a mammography imaging system to acquire hand images for assessing BMD can improve the workflow and access for women to BMD exams, so as to reduce the cost and improve the efficiency of screening.

Conventional x-ray imaging systems have been employed to image various human body parts (e.g., head, neck, chest, abdominal, and extremities) to detect and diagnose various diseases. Because of the bone structures and thick body part, high-energy x-ray is required to provide sufficient penetration. Also, a wide range of x-ray energies (for example, from 50 kVp-140 kVp, dependent on the selection of kVp) is available to provide a suitable x-ray photon energy level (kVps) when imaging different body parts. Tungsten targets are typically used in conventional systems to meet the needs of a wide-range of high energy x-rays. Generally, thicker and/or denser body parts require higher x-ray energy to provide sufficient penetration to achieve desired image quality while keeping the patient dose at minimum.

For example, 50-60 kVps are typically employed for extremities, 70-90 kVp for hip and skull, and 100-130 kVp for chest. The signal strength (i.e., the amount of x-rays) reaching the detector can vary for a given x-ray energy. The weakest image signals are typically behind or within the dense and thick body parts (i.e., high attenuation), such as bone or abdomen. The strongest image signals reaching the detector are in the area of cavities or thin body part (i.e., low attenuation), such as the clear lung area or low-density soft tissue.

However, there is a non-linear relationship between x-ray exposure (i.e., amount of x-rays) to the x-ray film and the film optical density (OD). Thus, neither underexposure (e.g., not enough penetration) or overexposure (e.g., too much x-rays penetrated the film) are desirable.

Figure 1:
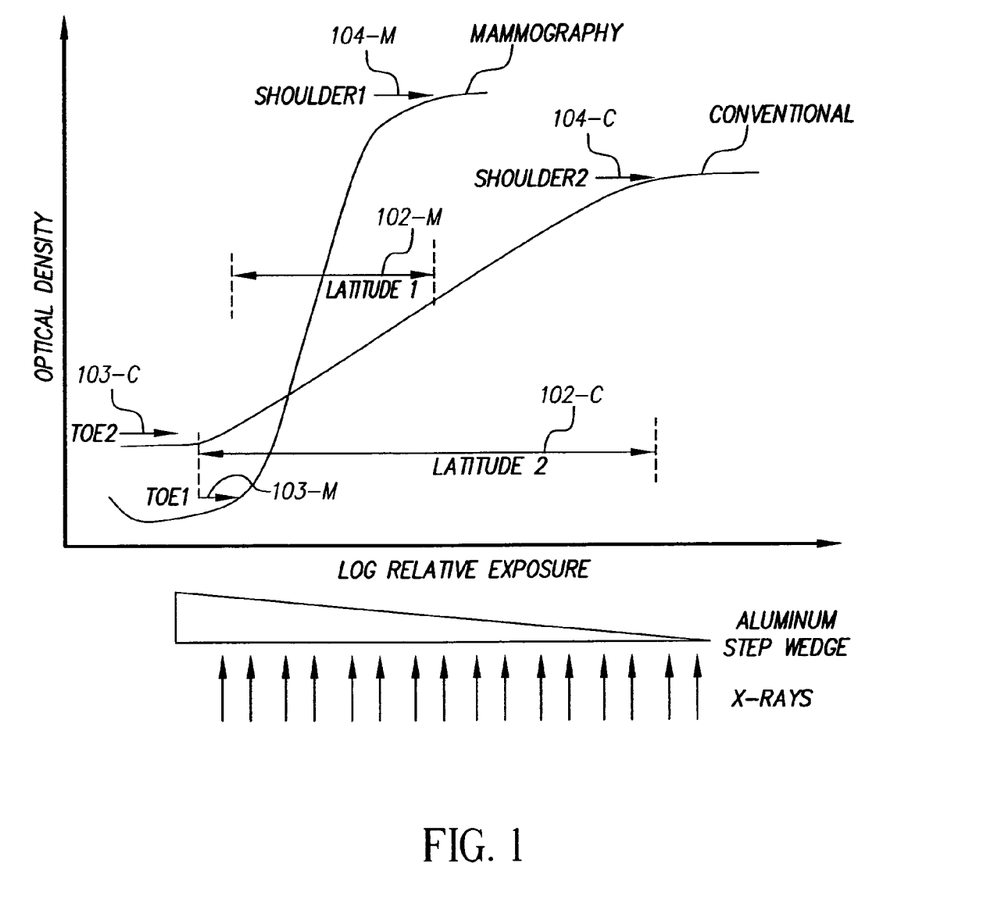
FIG. 1 shows a curve illustrating the relationship between the x-ray exposure (the amount of x-rays reaching the screen/film) and the film optical density (OD) for a mammography system and a conventional x-ray imaging system.

FIG. 1 illustrates the relationship between the x-ray exposure (the amount of x-rays reaching the screen/film) and the film optical density (OD). The curve is usually called the H&D curve which characterize the uniqueness of a screen/film system in its response to x-ray exposure. Two curves are shown in FIG. 1: one for a screen/film mammography system and one for a conventional screen/film x-ray imaging system. The two curves illustrate a difference in latitude 102 between the conventional and mammography screen/film systems, referenced as 102-C and 102-M, respectively. More particularly, FIG. 1 shows characteristics curves for a mammography screen/film system (e.g., high contrast, narrow latitude) and a conventional screen/film system (e.g., low contrast, wide latitude).

Latitude is defined as the wide linear range of the optical density over the exposure. That is, latitude refers to the range of relative exposure that will produce optical density within the accepted range for detection and diagnosis.

Information captured on the shoulder and beyond is referred to as overexposed 104, while information captured on the toe is referred to as underexposed 103. The wider latitude in conventional screen/film reduces the likelihood of overexposure or underexposure of films on the shoulder and toe. Such overexposure and underexposure are considered to be undesirable image quality. When undesirable images occur, a retake of the image is required to capture sufficient information for detection and diagnosis. Underexposure of the conventional and mammography screen/film systems is shown in FIG. 1 as 103-C and 103-M, respectively. Overexposure of the conventional and mammography screen/film systems is shown in FIG. 1 as 104-C and 104-M, respectively.

An x-ray film digitizer can be employed to convert an analog x-ray image to a digital image. Such x-ray film digitizers are well known.

Still referring to FIG. 1, only the signals (exposures) within a limited range (latitude 102) are visible or recognizable by an x-ray film digitizer. Because of the wide range of densities in the body parts, the range of image signals and their strength which reach the film is considerably wide. Therefore, conventional x-ray films are design to provide wide enough latitude 102 to properly capture a wide range of image signals on the film.

Mammography systems are designed to capture x-ray breast images, particularly for the detection and diagnosis of breast cancer. Since the attenuation or density differences in the different parts of breast tissues are small, mammography systems employ x-ray equipment and detectors specially designed to optimize breast cancer detection. Using low x-ray photon energies generally will provide better differential attenuation between the soft tissues than using higher energy x-ray photons (50 kVp and above). However, low x-ray energy has a high absorption and therefore delivers a relatively high dose.

Screen/film systems used in mammography are also designed to maximize the contrast for the captured image signals and require a certain of amount of radiation to ensure sufficient image quality for the cancer detection task.

Figure 2:
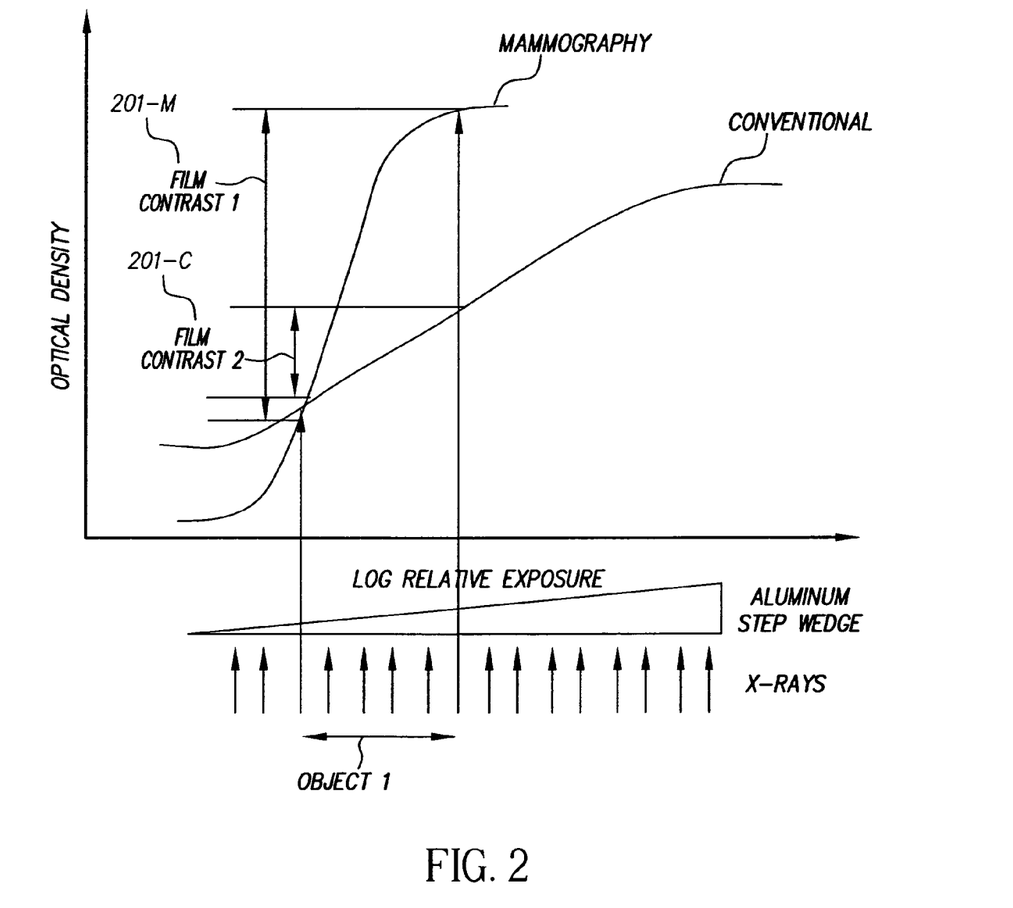
FIG. 2 shows a curve illustrating the difference in contrast between conventional systems and mammography systems.

Referring to FIG. 2 there is shown the H&D curves of a screen/film system for mammography and a screen/film system for conventional x-ray imaging system, illustrating the difference in contrast 201 between the conventional and mammography screen/film systems, referenced as 201-C and 201-M, respectively.

More particularly, FIG. 2 shows characteristic curves for a mammography screen/film system (e.g., high contrast, narrow latitude) and a conventional screen/film system (e.g., low contrast, wide latitude). The graph illustrates the difference in film contrast between the two types of screen/film systems for an object with the same object contrast. FIG. 2 was obtained by projecting object 1 (a portion of aluminum step wedge) within the proper exposure range for the mammography system, while the entire step wedge was captured within the wide dynamic latitude of the conventional screen/film system.

Minimizing the dose while providing sufficient image quality to enhance the low contrast detection imposes extreme requirements on mammographic equipment and detectors. Because of the risk of ionizing radiation, some prefer to minimize the dose and optimize the image quality. These concerns have led to the refinement of dedicated x-ray equipment, specialized x-ray tubes, compression devices, and/or optimized detector systems. The imaging requirements impact the design of the x-ray tube, peripheral mammographic equipments, and film/screen detectors.

X-ray tubes designed specially for mammography provide can provide a nearly optimal x-ray spectrum for a good subject contrast of soft tissues while maintaining a radiation dose as low as possible.

Some experiments have shown that for a tissue thickness having a 3-6 cm range (e.g., typical compressed breast thickness), preferred x-ray energies are typically generated through a molybdenum target with a kVp range between 24 to 32 kVp.

A maximum tube voltage of the x-ray source for mammography is approximately 45 kVp.

The x-ray source is defined by a target and filter combination (sometimes referred to as target/filter). Examples of target/filter combinations includes molybdenum/molybdenum, molybdenum/rhodium, rhodium/rhodium, and tungsten/rhodium.

The contradictory requirements of high subject contrast and low radiation dose are difficult to accomplish, and indicate mono-energetic x-rays as the best choice. However, x-ray energy of the x-ray tube is poly-energetic.

Figure 3:
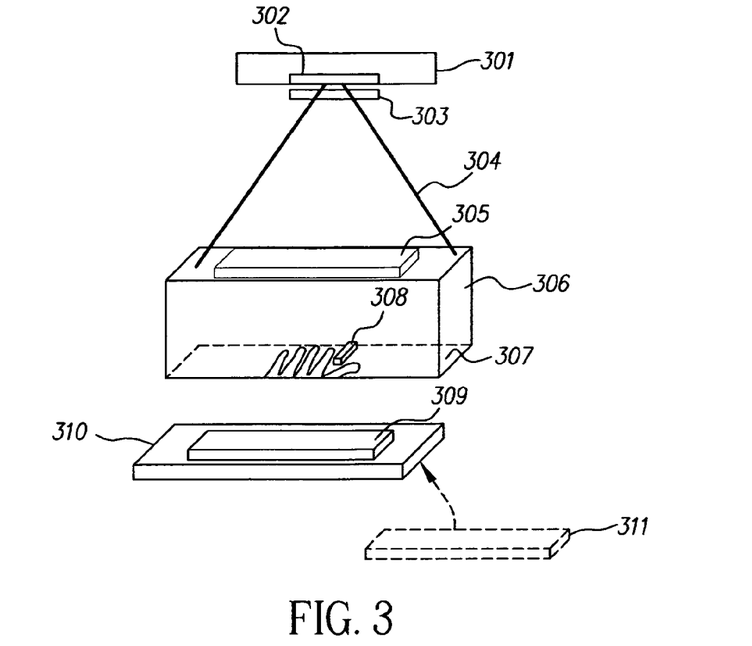
FIG. 3 illustrates the system in accordance with the present invention for obtaining hand images for BMD assessment using a mammography system.

Referring to FIG. 3, there is shown a system in accordance with the present invention for obtaining hand images for BMD assessment using a mammography system. A source 301 emits x-ray energy 304 directed toward an object to be imaged (shown as fingers/hand in FIG. 3). A hand template 307 can be provided to properly position the object. One or more phantom/calibration/step wedges 308 can be positioned proximate the object made of a material (e.g., aluminum) to approximate the density variations of a human extremity. Template 307 and wedge 308 can be positioned by frame 306.

Referring to FIG. 3, built-in filtration 302 is added to the x-ray tube to remove some of the low energy x-rays as the low energies contribute to tissue dose without contributing significantly to image formation. The highest x-ray energies in the x-ray beam are a function of the peak operating voltage (kVp) applied and added filtration at the x-ray tube port. A fixed amount of filtration (for example, molybdenum/rhodium) is built in the system to remove the low-energy x-rays. A rotating anode design is used for some mammographic x-ray tubes. Molybdenum targets are common, although tungsten is used in many tubes. A dual track molybdenum/rhodium target and molybdenum/rhodium filtration is used by a manufacturer.

A combination of target and filtration determines the x-ray beam quality, which in turn determines the image quality (contrast and exposure level).

The x-ray beam quality determined by the combination of the target and filtration in conjunction with the x-ray energy range (operating kVp range) provide a distinction between mammography x-ray systems and conventional x-ray systems, and this determines the difference in their applications.

With regard to the image detector, the beam quality determines how much signals can penetrate through different body parts with different thickness, reaching the detector. The characteristics of a detector (FIG. 1 and FIG. 2) determine the way in which the signals are captured and presented in an analog and/or digital format by the detector. Detectors are customized to the need for conventional x-ray systems and for mammography x-ray systems. As was shown in FIG. 1, a conventional screen/film system has a wider latitude 102-C to capture the wide range of signals in strength for imaging head, neck, chest, abdominal and extremities.

Hands can be imaged using conventional x-ray machines. The high x-ray energy in conventional x-ray machine provides sufficient penetration to see the details in the bone while the wide latitude of the screen/film system allows capture of both the soft tissues (low attenuation) and bone (high attenuation) in one image. As was shown in FIG. 1, information captured on the shoulder and beyond is referred to as overexposed (104-C and 104-M), while information captured on the toe is referred to as underexposed (103-C and 103-M). Both overexposure and underexposure are not desirable. The wider latitude in conventional screen/film reduces the likelihood of overexposure or underexposure of films on the shoulder and toe.

Mammography screen/film systems have a higher contrast than conventional screen/film systems. This was illustrated in FIG. 2, where the difference in optical density on the vertical axis is used to measure the film. For example, an aluminum step wedge is an object having varying attenuation. The thicker the step wedge, the more x-rays are attenuated, and accordingly, the less x-rays reach the film. For a given object contrast (difference in exposure along horizontal axis in FIG. 2), the film contrast 201 for mammography screen/film is higher than that for conventional screen/film system. While the high contrast in mammography screen/film detectors assists to signify the small difference among the soft tissues in a breast, the narrow latitude 102 allows it to capture the information from a portion of the aluminum step wedge. It is difficult to capture both soft tissues and high-density bone structure on one single image. One can increase or decrease the x-ray energy and x-ray intensity to project the desired portion of the aluminum step wedge into the narrow latitude. For example, one can increase the x-ray energy to increase the exposure to the film under the thicker part of the aluminum, so that the thicker part of the aluminum got exposed properly within the narrow latitude. Note that when the thicker part of the aluminum gets exposed properly, the portion of aluminum at the thin end likely gets overexposed. This indicates that overexposure of soft tissue or underexposure of bone is likely to occur when a mammography screen/film detector is used.

It is well known to use a cassette to hold a screen/film for x-ray imaging. If the screen/film employs a phosphor storage phosphor material (such as used for computed radiography), the storage phosphor screen/film can be disposed within a cassette for imaging. FIG. 3 generally shows a cassette 310 which can house computed radiography plate 311 (having a storage phosphor layer). Cassettes designed for mammography can include some particular attributes. Some cassettes are made of a low attenuation carbon fiber and/or have a single high definition screen used with a single emulation film.

Because of the difference in the requirement for the x-ray beam quality between mammography and conventional x-ray image systems, and in the requirement for characteristics of screen-film detectors between the two systems, it is difficult to image hands using a low-energy (i.e., mammography) x-ray beam quality system to get sufficient penetration of the bone while not overexposing the soft tissues in the hand.

For an accurate assessment of BMD using hand x-ray images, a sufficient amount of soft tissue needs to be visible as well as the detailed bone trabecular structures. Overexposing the soft tissue or under exposing the bone structure on the films can easily occur if proper techniques are not used to image the hands. These techniques include the right choice of target/filtration combination, additional filtration provided by attenuation filter material in-between the target to imaged object (hand), additional attenuation filter material in-between imaged object to the image receiver, speed and latitude of screen/film system.

Since mammography is particularly designed for breast imaging, the limits or constraint set on how the system can be used does limit the choices of the kVp and mAs combinations along with other factors to capture the right exposure for hands. For example, 1) the maximum x-ray energy from mammography system is set at 45 kVp for rhodium target and 35 kVp for molybdenum target. This constriction limits the choices to use higher energy x-rays to get a good penetration of bone. 2) A low limit set on the output (x-ray intensity) for mammography x-ray units is rather high (4 or 5 mAs), it often causes overexposure to the soft tissue on hand image. 3) The distance from the source (target) to image receiver on mammography system is often fixed (65 cm), so the x-ray radiation cannot be lowered by increasing the distance, which is a way often used in conventional x-ray system to lower intensity of the x-ray radiation reach the film. A suggested distance between target and image receiver for imaging hands is 40 inches.

As mentioned above, a high kVp is employed to obtain a good penetration of the hand. However, when kVp increases for a selected mAs setting, the radiation output (exposure to the film) increases as more x-rays are able to penetrate the object. To avoid overexposure of the soft tissue, it is desired to reduce the amount of the exposure to the film by reducing the mAs and increasing the distance from the source to the detector. As a result of these limitations on the high-end kVp, minimum mAs and the fixed distance from source to receiver on the mammography systems, when good penetration is obtained, soft tissue is often overexposed. Conversely, when soft tissue is appropriately imaged, sufficient penetration of bone cannot be reached. These limitations aggregated the problem in finding the right techniques to appropriately image the hand using mammography x-ray image systems and/or mammography screen/film detectors.

To address the various problems discussed above, Applicants have replaced the mammography screen/film detectors with digital detectors, that is, direct digital radiography (DR) and computed radiography (CR) designed for mammography. These detectors generally have a wide dynamic range of the pixel value over the exposure levels. With a combination of high x-ray energy (kVps) and mAs on the mammography machine, a suitable image quality for both soft tissue and bone detail has been obtained. Note that cassettes for mammography can be used to hold a CR screen when CR detectors are used.

Further, the mammography screen/film system was replaced with low speed (<150) conventional screen/film detectors. For example, film designed for general radiography, such as Kodak X-sight G/RA, X-sight L/RA film, TMAT G/RA film or TMAT L/RA film or Insight film family. These detectors, as mentioned above, have wider latitude than mammography screen/film system. The screen/film were placed into a mammography cassette and positioned for imaging (for example, inserted into a bucky).

Using the x-ray energy of a mammography system and the conventional screen/film system allowed Applicant to generate hand images with sufficient good image quality for BMD assessment.

Further, mammography films can be replaced with conventional radiography films (with speed of slower than 400). Thus the combination of a mammography screen and a conventional radiography film was used to acquire hand images.

Further, the screen/film configuration in terms of its position relative to incoming x-rays direction was investigated. In mammography, a single back screen configuration (i.e., placing the film between the x-ray source and the screen) is often used to maximize the image sharpness and the efficiency of the screen in converting absorbed x-ray energy to light. For imaging a hand using mammography, a single front screen configuration can be used to reduce the x-ray to light conversion efficiency of the screen to avoid overexposure to the hand tissue. That is, the screen is placed between the x-ray source and the film. Examples of a mammography screen/film system which can be used in the front screen configuration are Kodak MinR screen or MinR 2000 screen or MinR 2190 screen or MinR 2250 screen or MinR EV screens with MinR-L film or MinR 2000 film or MinR EV film. Screens designed for conventional radiography such as Lanex fine screen, Lanex medium screen, Lanex regular, Lanex Fast (Lanex screen family) or Insight screen family can replace the screen designed for mammography in either a back screen or front screen configuration.

Some images acquired in the configurations described above have been reviewed using an available computer-aided BMD assessment system. (Note the computer-aided assessment system was originally designed to assess the BMD using the hand images acquired from conventional x-ray machines with the conventional screen-film system (U.S. Pat. No. 6,246,745)). The computer-aided assessment system relates to input images acquired using x-ray energies of 50 kVp and above and background optical density (OD) on the film of 1.0−/+0.1. The background OD obtained from the above configuration is higher than 1.0 because the constraints set on kVp, mAs, distance from the source to detector and the choice of the target/filtration combination. From the results, Applicants believe that low energy x-ray beams from mammography x-ray systems when combined with a detector with sufficient wide latitude in its H&D curve can generate hand images with adequate image quality for BMD assessment.

Applicants investigated using mammography screen/film systems as detectors to capture hand images for BMD assessment recognizing that there are limitations on the mammography x-ray imaging systems and the property of mammography screen/film designed breast imaging, and that there are numerous combinations of multiple variables (choice of target/filtration, added material for additional filtration, kVps, mAs, screen/film combinations). Mammography screen/film system were categorized into two categories, high and low contrast. Hand phantom images with sufficient penetration of bone and sufficient soft tissue required by the software can be achieved with selections of target/filtration combination, kVp and mAs, positioning of hands, additional filtration, and types of screen/film.

At 4 mAs setting when the images were acquired using a high-contrast screen/film (Kodak MinR EV system), the acceptable kVp range (which generates acceptable image quality for BMD assessment) is between 31 and 35 for molybdenum/molybdenum target-filtration combination, is between 30 and 34 for molybdenum/rhodium combination target-filtration combination, and is between 29 and 32 for rhodium/rhodium combination target-filtration combination. Tungsten/rhodium combinations also may be used.

When increasing mAs setting from 4 mAs, the acceptable kVp range was shifted to a lower kVp range. Both the lower and upper bound kVp values reduced a rate of 1 or 2 kVp per mAs. This results since the radiation exposure increases as the mAs increases at a given x-ray energy setting (kVp). An acceptable kVp range may get smaller at a higher energy as there is minimum kVp setting for each target/filtration combination. The minimum kVp for molybdenum/rhodium is 24. The minimum kVp for rhodium/rhodium is 25.

When a low-contrast mammography screen/film system was used (e.g., Kodak MinR L), the acceptable kVp range at each corresponding mAs setting is wider than that for the high contrast screen/film system. However, the minimum acceptable kVp at each mAs setting is similar to that of the high-contrast screen/film system. Thus minimum x-ray energy (kVp) is required, regardless of the type of screen/film combination, to have the penetration of bone required for BDM analysis.

Further, additional filtration provided by attenuation filter material can be placed between the hand and the x-ray source target to reduce or attenuate the amount of x-ray radiation, thus avoiding overexposure for the soft tissue, especially at higher kVps.

While this can reduce the output to avoid overexposure of soft tissue by adding an additional attenuation filter to the built-in filtration, this can further increase the penetration of the bone by using higher energy x-rays. A wider range of kVps can be employed to generate the hand images with sufficient image quality, thus increasing the robustness of its implementation. It is known that different mammography x-ray units are calibrated differently. In addition, the thickness and size of hands can vary. A wider range of kVps can increase the robustness of the system to generate images for accurate assessment of BMD by the computer system.

The additional attenuation filter materials can be aluminum of thickness between 0.02 to 12 mm, polymethyl methacrylate of thickness between 0.5 to 120 mm, copper 0.001 to 0.4 mm or other material with the thickness ranges that can provide the x-ray intensity attenuation from 5% to 99.9% of the x-ray intensity without additional filter material.

Further, additional attenuation filter material can also be placed between the hand and the screen film system to further attenuate the amount of x-rays to avoid overexposures to the film. This can also be achieved by using thicker or high attenuation material for the front cover of the screen film cassette.

Use of grid in the Bucky can be applied to reduce the x-ray exposure to the film.

When hand images are acquired using conventional x-ray units along with a conventional screen/film system, a desktop scanner can be employed. For images acquired using mammography x-ray units, a x-ray film digitizer with a wide dynamic latitude can be used to read the wide range of information captured on the mammography film. The sufficient dynamic latitude is defined as the Dmin (minimum optical density) and Dmax (maximum optical density) recognizable by the digitizer. Dmin of 0.2 and Dmax of 4.0 have been recommended to capture the details required for the computer analysis.

When acquiring the images, the patient stands on the chest wall side of the mammography system facing the gantry. One hand is positioned on a template with an aluminum step wedge placed proximate the thumb and the index finger (for example, refer to U.S. Pat. No. 6,246,745 (Bi)). The hand is positioned to lay flat on the template.

Figure 5:
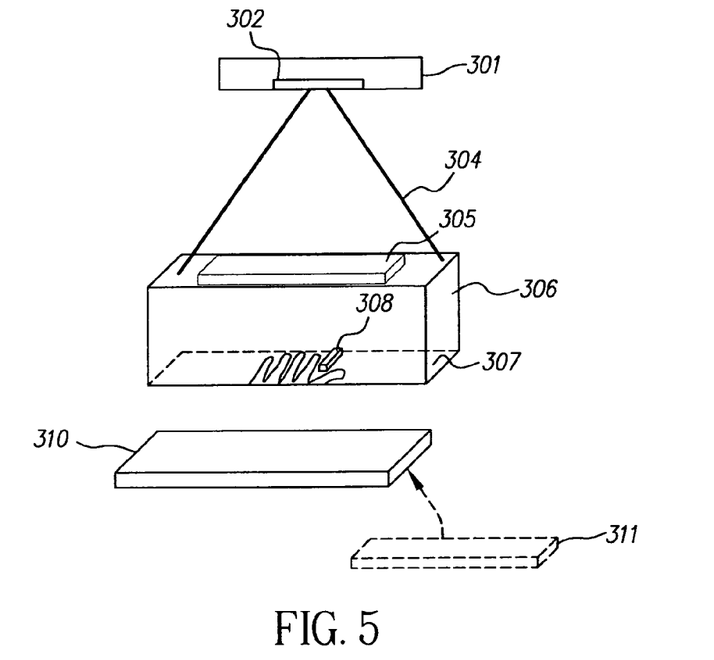
FIG. 5 illustrates the system in accordance with the present invention wherein filtration is added proximate the support supporting the body extremity.

As shown in FIGS. 3 and 5, frame 306 with the hand template 307 placed at the bottom and the additional attenuation filter material 305 placed on the top can be used to position the hand when additional filtration is required to get adequate image quality.

Although, the added materials for additional attenuation filter 305 is preferred to be placed in between anode/target and imaged object, another way to add filtration is to place the material on the breast compression plate attached to the mammography x-ray unit or simply use the compression plates. Another way is to mount the filter material on a support that can be attached to the mammography machine the same way as the compression plate does. Another way is to attach the add-on attenuation filter 303 on the x-ray exit window of the x-ray tube.

Figure 4:
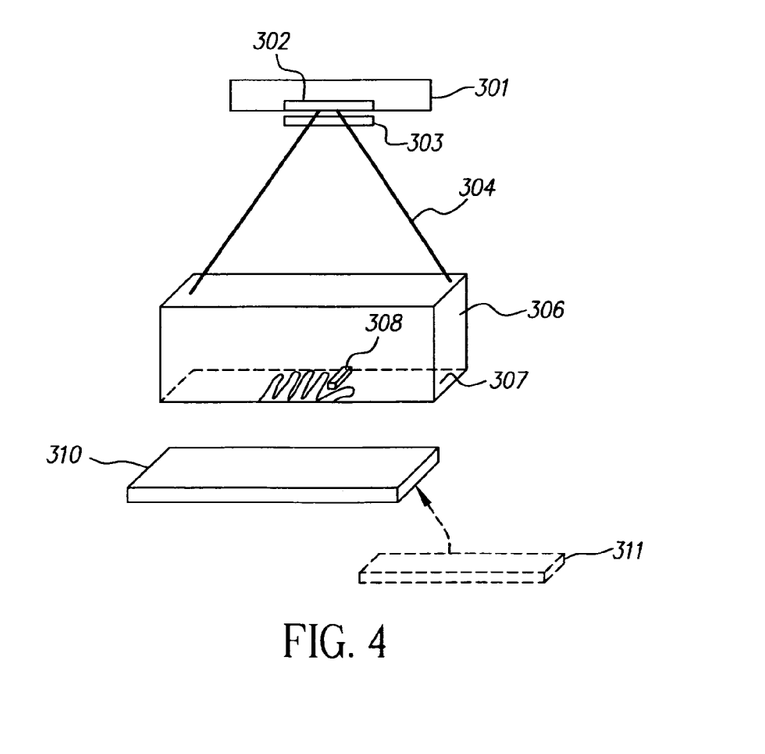
FIG. 4 illustrates the system in accordance with the present invention wherein filtration is added proximate the x-ray source.
Figure 6:
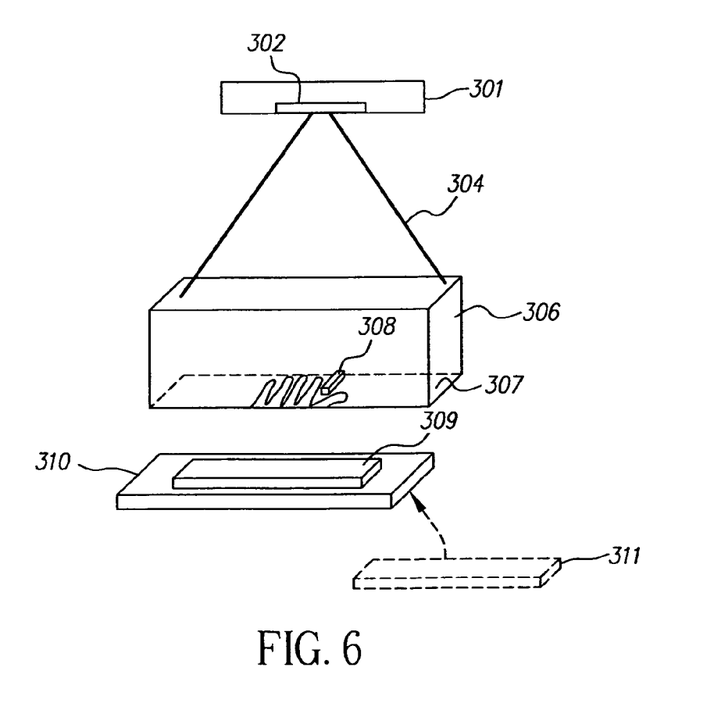
FIG. 6 illustrates the system in accordance with the present invention wherein filtration is added proximate the detector.

With reference to FIG. 4, additional attenuation filter 303 can be added proximate x-ray source 301. Alternatively, as shown in FIG. 5, additional attenuation filter 305 can be added proximate frame 306. Still further, as shown in FIG. 6, additional attenuation filter 309 can be added to cassette 310. Combinations of these can also be employed. For example, FIG. 3 shows the use of added attenuation filters 303, 305, and 309.

The acquired hand images can be evaluated by a computer or a treating physician for BMD assessment purpose. The image quality can be evaluated by a computer system. The system uses a step wedge for a calibration purpose. The system can employ a test procedure to assess if sufficient image quality (sufficient soft tissue and adequate penetration of bone) is achieved. Other systems may have different requirements in image quality. However, the calibration for adequate penetration and/or sufficient soft tissue ensures the accurate assessment of BMD. The present invention provides a method to acquire digital hand images using mammography x-ray system for the purpose of BMD assessment.

Thus, the present invention provides a method of acquiring hand x-ray images. According to one aspect of the present invention, the method comprises the steps of generating a digital or analog x-ray radiograph of human hand using mammography imaging system. A cassette and screen is used wherein having a MO/MO or MO/Rh target/filter combination (MO being molybdenum, and Rh being rhodium) with exposure level lower than 10 mAs. In one arrangement, a phosphor screen/film combination is inserted into a cassette to hold screen and film for x-ray imaging.

According to another aspect of the present invention, there is provided a system to acquire hand images on a radiograph using a mammography x-ray system. The system includes x-ray generator with rotating targets and filtration materials designed for mammography, image receivers and additional filtration.

The invention claimed is:

1. A radiographic imaging system for capturing an image of a body extremity which is suitable for determining a bone mineral density, the system comprising:
   a support for supporting the body extremity;
   an x-ray source configured to project an x-ray beam through the body extremity, the x-ray source having a voltage of no more than 45 kVp and having a target/filter combination of rhodium/rhodium, molybdenum/molybdenum, molybdenum/rhodium, or tungsten/rhodium;
   a detector configured to receive the x-ray beam after the x-ray beam passes through the body extremity and to capture an image of the body extremity;
   an attenuation filter separate from the target/filter combination of the x-ray source and positioned between the x-ray source and detector, the attenuation filter configured to attenuate a low-energy portion of the x-ray beam; and
   a processor configured to determine a bone mineral density of the body extremity based on the image of the body extremity captured by the detector.

2. The radiographic imaging system of claim 1, wherein the detector is a cassette housing conventional general radiography film.

3. The radiographic imaging system of claim 1, wherein the detector is a cassette housing mammography radiography film.

4. The radiographic imaging system of claim 1, wherein the attenuation filter is positioned between the x-ray source and the body extremity proximate the x-ray source.

5. The radiographic imaging system of 1, wherein the attenuation filter is selected from the group consisting of: aluminum having a thickness of between 0.02 to 12 mm; polymethyl methacrylate having a thickness between 0.5 to 120 mm; and copper having a thickness between 0.001 to 0.4 mm.

6. The radiographic imaging system of claim 1, wherein the attenuation filter is position between the x-ray source and the body extremity proximate the body extremity.

7. The radiographic imaging system of claim 1, wherein the attenuation filter is comprised of a material of a thickness range which provides x-ray intensity attenuation from 5% to 99.9% of the x-ray intensity without the attenuation filter.

8. The radiographic imaging system of claim 1, wherein the detector comprises a digitally-based detector.

9. The radiographic imaging system of claim 8, wherein the digitally-based detector comprises a computed radiography plate comprising a storage phosphor material.

10. The radiographic imaging system of claim 8, wherein the detector is a direct digital radiography (DR) detector.

11. A radiographic imaging system for determining the bone mineral density of a body extremity, comprising:
    a support for supporting the body extremity;
    a detector for capturing a digital image of the body extremity;
    an x-ray source adapted to project an x-ray beam through the body extremity toward the detector, the x-ray source having a voltage of no more than 45 kVp and having a target/filter combination of rhodium/rhodium, molybdenum/molybdenum, molybdenum/rhodium, or tungsten/rhodium; and
    a processor configured for processing the captured digital image to determine the bone mineral density of the body extremity, based on the image of the body extremity captured by the detector.

12. A method for providing an image of a body extremity suitable for a bone mineral density analysis using a mammography radiographic imaging system, the method comprising:
    positioning the body extremity on a support of the mammography radiographic imaging system;
    projecting an x-ray beam through the body extremity from an x-ray source of the mammography radiographic imaging system, the x-ray source having a voltage of no more than 45 kVp and a target/filter combination of rhodium/rhodium, molybdenum/molybdenum, molybdenum/rhodium, or tungsten/rhodium;
    capturing an image of the body extremity on a detector by receiving the x-ray beam with the detector after the x-ray beam passes through the body extremity;
    positioning an attenuation filter between the x-ray source and the detector to filter a low-energy portion of the x-ray beam; and
    employing a processor to determine a bone mineral density of the body extremity based on the captured image of the body extremity.

13. The method of claim 12, wherein the attenuation filter is comprised of a material of a thickness range which provides x-ray intensity attenuation from 5% to 99.9% of the x-ray intensity without the attenuation filter.

14. The method of claim 12, wherein positioning the attenuation filter includes selecting the attenuation filter from a group consisting of: aluminum having a thickness of between 0.02 to 12 mm; polymethyl methacrylate having a thickness between 0.5 to 120 mm; and copper having a thickness between about 0.001 to 0.4 mm.

15. The method of claim 12, wherein capturing the image of the body extremity on the detector includes employing a detector comprising a digitally-based detector.

16. The method of claim 15, wherein the digitally-based detector comprises a computed radiography plate comprising a storage phosphor material.

17. The method of claim 15, wherein the digitally-based detector comprises a direct digital radiography (DR) detector.

18. The method of claim 12, wherein capturing the image of the body extremity on the detector includes employing a detector comprising a cassette housing conventional general radiography film.

19. The method of claim 12, wherein capturing the image of the body extremity on the detector includes employing a detector comprising a cassette housing mammography radiography film.

20. A method for providing an image of a body extremity suitable for a bone mineral density analysis using a mammography radiographic imaging system, the method comprising:
    positioning the body extremity on a support of the mammography radiographic imaging system;
    projecting an x-ray beam through the body extremity from an x-ray source of the mammography radiographic imaging system, the x-ray source having a voltage of no more than 45 kVp and a target/filter combination of rhodium/rhodium, molybdenum/molybdenum, molybdenum/rhodium, or tungsten/rhodium;
    positioning an attenuation filter, between the x-ray source and a detector of the imaging system and between the body extremity and the detector, to filter a low energy portion of the x-ray beam that has passed through the body extremity; and
    capturing an image of the body extremity on the detector by receiving the x-ray beam with the detector after the x-ray beam passes through the body extremity and the attenuation filter.

* * * * *